US006340419B1

(12) United States Patent
Nakae et al.

(10) Patent No.: US 6,340,419 B1
(45) Date of Patent: Jan. 22, 2002

(54) MULTILAYERED AIR-FUEL RATIO SENSING ELEMENT

(75) Inventors: Makoto Nakae, Toyoake; Tomio Sugiyama, Nagoya, both of (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/379,914

(22) Filed: Aug. 24, 1999

(30) Foreign Application Priority Data

Aug. 25, 1998 (JP) ............................................ 10-238794

(51) Int. Cl.⁷ .............................................. G01N 27/407
(52) U.S. Cl. ........................ 204/429; 204/426; 204/427; 156/89.12; 156/89.16
(58) Field of Search ................................ 204/421–429

(56) References Cited

U.S. PATENT DOCUMENTS 4,859,307 A * 8/1989 Nishizawa et al. ......... 204/425

FOREIGN PATENT DOCUMENTS

| JP | 60-13256 | 1/1985 |
| JP | 63-307352 | 12/1988 |
| JP | 4-120454 | 4/1992 |

* cited by examiner

*Primary Examiner*—T. Tung
(74) *Attorney, Agent, or Firm*—Pillsbury Winthrop LLP

(57) ABSTRACT

A multilayered air-fuel ratio sensing element comprises a solid electrolytic substrate having oxygen ion conductivity. A measuring gas sensing electrode is provided on one surface of the solid electrolytic substrate so as to be exposed to a measuring gas. A reference gas sensing electrode is provided on another surface of the solid electrolytic substrate so that the reference gas sensing electrode is exposed to a reference gas introduced into a reference gas chamber. The measuring gas sensing electrode is covered by a porous diffusive resistor layer. And, a hollow space is provided between the measuring gas sensing electrode and the porous diffusive resistor layer.

9 Claims, 11 Drawing Sheets

COMPARATIVE EXAMPLE

COMPARATIVE EXAMPLE

COMPARATIVE EXAMPLE

COMPARATIVE EXAMPLE
REACHING WITH DIFFERENT TIME LAG

TEMPORARILY STORED AND UNIFORMLY MIXED

MULTILAYERED AIR-FUEL RATIO SENSING ELEMENT

BACKGROUND OF THE INVENTION

The present invention relates to a multilayered air-fuel ratio sensing element which detects the emission gas concentration in an exhaust gas passage to control the air-fuel ratio of an internal combustion engine installed in an automotive vehicle or the like.

To purify the harmful emission components included in the exhaust gas of the internal combustion engine and also to improve the fuel economy of the internal combustion engine, an air-fuel ratio sensor is conventionally used to feedback control the combustion in the internal combustion the engine. A multilayered sensing element is preferably installable in such an air-fuel ratio sensor.

In general, the multilayered air-fuel ratio sensing element comprises a solid electrolytic substrate having oxygen ion conductivity, an emission gas sensing electrode provided on one surface of the solid electrolytic substrate, and a reference gas sensing electrode provided on the other surface of the solid electrolytic substrate. A surface of the emission gas sensing electrode is covered by a diffusive resistor layer with numerous pin holes allowing the emission gas to diffuse therein (refer to the unexamined Japanese patent publication 4-120454). The diffusive resistor layer functions as a diffusion rate-determining layer.

The multilayered air-fuel ratio sensing element detects an air-fuel ratio based on the current flowing between the emission gas sensing electrode and the reference gas sensing electrode when a predetermined voltage is applied between these electrodes.

The emission gas sensing electrode has catalytic activity for ionizing oxygen involved in the emission gas in response to the voltage applied between the emission gas sensing electrode and the reference gas sensing electrode. The ionized oxygen moves in the solid electrolytic substrate and reaches the reference gas sensing electrode. The ionized oxygen flow causes ion current between the two electrodes. The diffusive resistor layer suppresses the diffusion speed of the emission gas.

FIG. 14 shows the relationship between the applied voltage and the resultant current measured when the voltage is applied between the emission gas sensing electrode and the reference gas sensing electrode. As apparent from FIG. 14, the increase of the current is not always proportional to the increase of the voltage. In a specific voltage range, the current remains constant irrespective of the increase of the voltage. In other wards, a flat region appears. In general, the saturated current value in this flat region is referred to as "limit current" value. Hereinafter, the flat region is referred to as "limit current" region.

The limit current value is variable depending on the air-fuel ratio as understood from FIGS. 14 and 15. In other words, the air-fuel ratio is detectable by setting the applied voltage so as to detect the limit current.

However, the diffusive resistor layer with numerous pin holes has temperature dependency in its diffusion performance. Using such a temperature dependent diffusive resistor layer is not preferable in view of the deterioration in the measuring accuracy of the multilayered air-fuel ratio sensing element. For example, when the air-fuel ratio remains constant, there is the possibility that the limit current of the multilayered air-fuel ratio sensing element may erroneously vary due to temperature change.

One of recent requirements to be realized for the advanced automotive engines is to realize a precise engine combustion control. To this end, prompt activation of the air-fuel ratio sensor is essentially important in an engine startup condition.

The multilayered air-fuel ratio sensing element starts its sensing operation only when the temperature exceeds its activation temperature. There is a significant dead time until the temperature reaches the activation temperature in the engine startup condition. To eliminate such a dead time, the multilayered air-fuel ratio sensing element is generally equipped with a heater to warm up the sensor body as quickly as possible.

To realize prompt activation of the multilayered air-fuel ratio sensing element, it is effective to downsize the sensor body so as to reduce the overall thermal capacity. However, the downsizing is limited to a certain degree. For example, the electrode area and the diffusive resistor layer thickness cannot be reduced so much to maintain or assure the sensor performances.

Furthermore, when the diffusive resistor layer is used, the sensing current may vary in response to fluctuation of the power source voltage applied to the multilayered air-fuel ratio sensing element.

SUMMARY OF THE INVENTION

An object of the present invention is to provide a multilayered air-fuel ratio sensing element which is compact in size and is capable of detecting the air-fuel ratio accurately irrespective of the temperature change or the power source voltage change.

In order to accomplish this and other related objects, a first aspect of the present invention provides a multilayered air-fuel ratio sensing element comprising a solid electrolytic substrate having oxygen ion conductivity, a measuring gas sensing electrode provided on one surface of the solid electrolytic substrate so as to be exposed to a measuring gas, a reference gas sensing electrode provided on another surface of the solid electrolytic substrate so that the reference gas sensing electrode is exposed to a reference gas introduced into a reference gas chamber, and a porous diffusive resistor layer covering the measuring gas sensing electrode. And, a hollow space is provided between the measuring gas sensing electrode and the porous diffusive resistor layer.

According to preferable embodiments of the present invention, the hollow space has a volume of 0.2 to 3.0 mm$^3$ per 10 mm$^2$ surface area of the measuring gas sensing electrode. The porous diffusive resistor layer has a porous rate of 3 to 15%. At least part of a surface of the porous diffusive resistor layer is covered by a gas shielding layer. The gas shielding layer is provided at a position opposing to the measuring gas sensing electrode. The gas shielding layer is made of a gas-impervious ceramic. The gas shielding layer extends along a surface of the porous diffusive resistor layer in an opposed relationship with the measuring gas sensing electrode via the porous diffusive resistor layer, so that the measuring gas introduced into the porous diffusive resistor layer flows in parallel with the gas shielding layer and reaches the measuring gas sensing electrode via the hollow space. The hollow space has a height in a range of 20 to 150 μm. The porous diffusive resistor layer is fabricated by laminating a green sheet on the solid electrolytic substrate and sintering an integrally laminated body.

Another aspect of the present invention provides a method for manufacturing a multilayered air-fuel ratio sensing element. The manufacturing method comprises the steps of preparing a plurality of green sheets to fabricate a solid electrolytic substrate, a spacer and a porous diffusive resistor layer, laminating the plurality of green sheets successively to form an integrated multilayered body with a hollow space between the solid electrolytic substrate and the porous diffusive resistor layer, and sintering the integrated multilayered body.

Preferably, the manufacturing method further comprises a step of additionally laminating a green sheet serving as a gas shielding layer on the porous diffusive resistor layer before the integrated multilayered body is sintered.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

Figure 1:
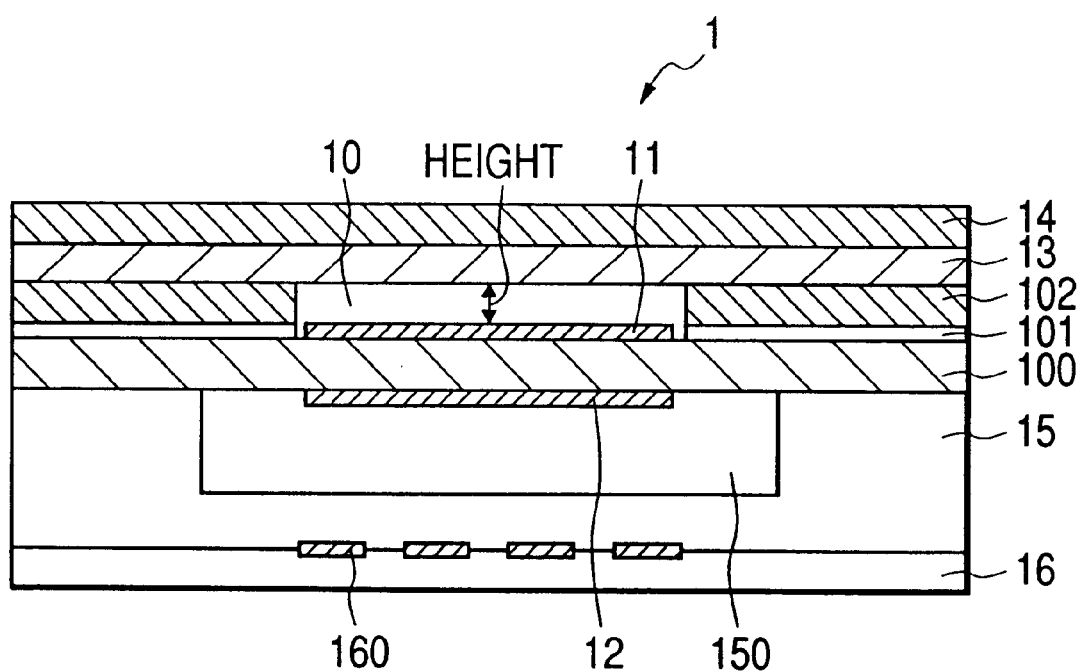
FIG. 1 is a lateral cross-sectional view showing an arrangement of a multilayered air-fuel ratio sensing element in accordance with a preferred embodiment of the present invention.

Preferred embodiments of the present invention will be explained hereinafter with reference to attached drawings. Identical parts are denoted by the same reference numerals throughout the views.

FIGS. 1–6 and 9–12 show preferred embodiments of the multilayered air-fuel ratio sensing element in accordance with the present invention. The multilayered air-fuel ratio sensing element is installable in an engine exhaust passage to measure the air-fuel ratio of an internal combustion engine.

Figure 2:
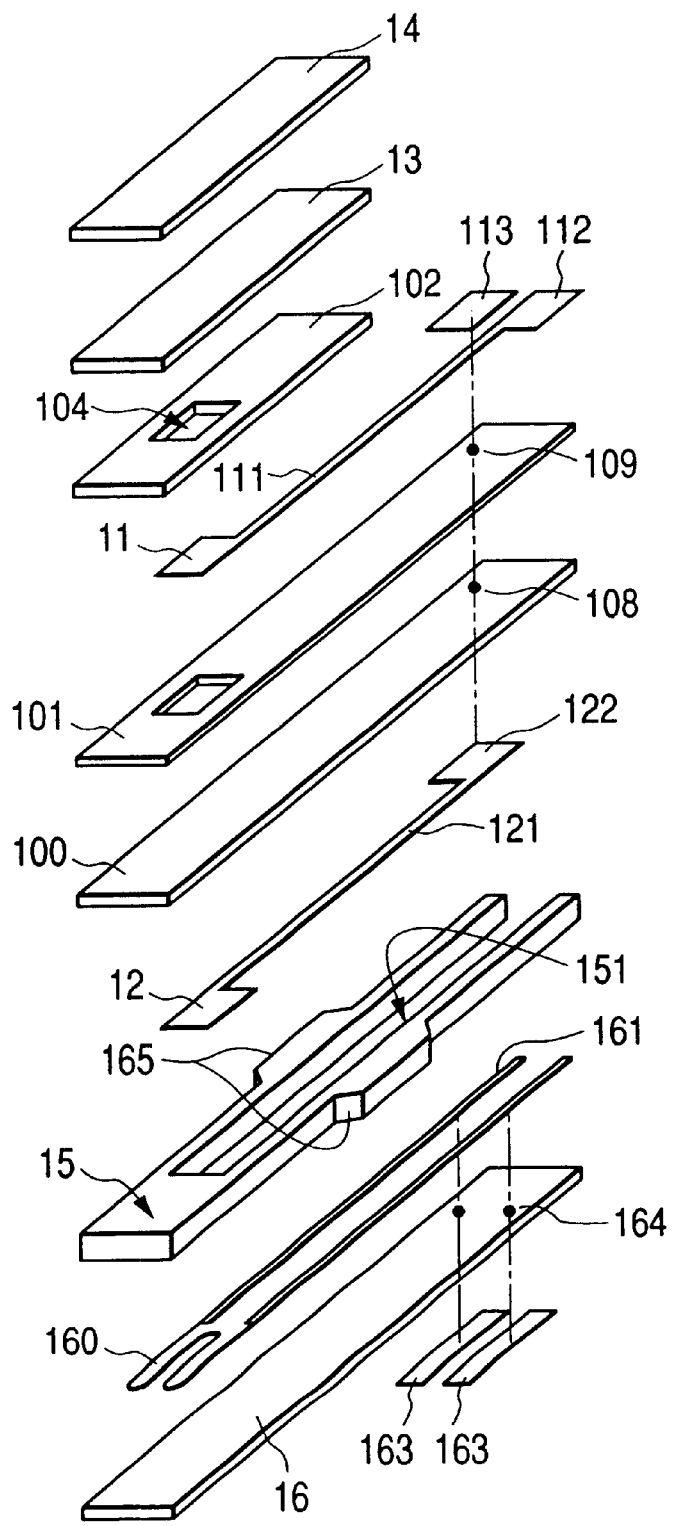
FIG. 2 is a development showing the multilayered air-fuel ratio sensing element shown in FIG. 1.

As shown in FIGS. 1 and 2, a multilayered air-fuel ratio sensing element 1 comprises a solid electrolytic substrate 100 having oxygen ion conductivity, an emission gas sensing electrode 11 provided on one surface of the solid electrolytic substrate 100, and a reference gas sensing electrode 12 provided on the other surface of the solid electrolytic substrate 100. The reference gas sensing electrode 12 is exposed to the reference gas introduced into a reference gas chamber 150. The emission gas sensing electrode 11 is covered by a porous diffusive resistor layer 13.

Figure 3A:
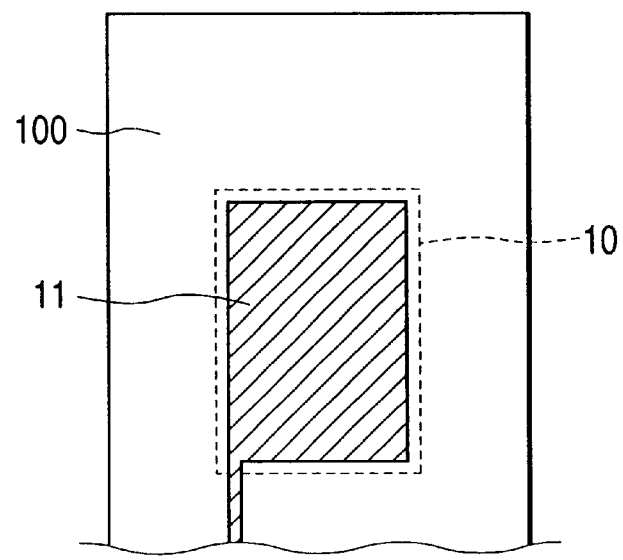
FIGS. 3A and 3B are views each showing the relationship between an emission gas sensing electrode and a hollow space in accordance with a preferred embodiment of the present invention.

A hollow space 10 is provided between the emission gas sensing electrode 11 and the porous diffusive resistor layer 13. The hollow space 10, i.e., a closed space, has a transverse area parallel to the emission gas sensing electrode 11 and slightly wider than a surface area of the emission gas sensing electrode 11. When seen from the direction normal to the surface of the emission gas sensing electrode 11 as shown in FIG. 3A, each side of the hollow space 10 protrudes outward from the corresponding side of the emission gas sensing electrode 11. Thus, the emission gas sensing electrode 11 completely overlaps with the hollow space 10.

The multilayered air-fuel ratio sensing element 1 is 60 mm in an overall longitudinal length and 2 mm in an overall thickness. The emission gas sensing electrode 11 has a surface area of 10 mm². The reference gas sensing electrode 12 has a surface area of 10 mm². The solid electrolytic substrate 100 has a thickness of 160 μm. The porous diffusive resistor layer 13 has a thickness of 200 μm. The multilayered air-fuel ratio sensing element 1 is sufficiently compact to realize the prompt activation.

The hollow space 10 has a volume of 0.3 mm³ with a height of 30 μm.

More specifically, as shown in FIGS. 1 and 2, an insulating layer 101 is provided on the upper surface of the solid electrolytic substrate 100. The insulating layer 101 is made of an alumina which is gas-impervious. The solid electrolytic substrate 100 is made of a partially-stabilized zirconia. The emission gas sensing electrode 11, made of a platinum, is provided on the upper surface of the solid electrolytic substrate 100. A lead 111 and a terminal 112, connected to the emission gas sensing electrode 11, are provided on the upper surface of the insulating layer 101.

A spacer 102 is stacked on the solid electrolytic substrate 100 which is assembled with the insulating layer 101, the emission gas sensing electrode 11, the lead 111 and the terminal 112. The spacer 102 is made of an alumina ceramic which is an electrically insulating and gas-imperious material. The spacer 102 has an aperture 104 defining the hollow space 10.

The porous diffusive resistor layer 13 is stacked on the spacer 102. The porous diffusive resistor layer 13 is made of an alumina ceramic having a porous rate (i.e., porosity) of 10%. Besides the alumina ceramic, the porous diffusive resistor layer 13 can be made of other ceramic, such as zirconia or $Al_2O_3$—MgO spinel.

A gas shielding layer 14 is stacked on the porous diffusive resistor layer 13. The gas shielding layer 14 is made of an alumina ceramic which has gas shielding ability.

The reference gas sensing electrode 12 is provided on an opposite (i.e., lower) surface of the solid electrolytic substrate 100. In other words, the reference gas sensing electrode 12 is opposed to the emission gas sensing electrode 12 via the solid electrolytic substrate 100. The reference gas sensing electrode 12 is made of a platinum. A lead 121 and a terminal 122, connected to the reference gas sensing electrode 12, are also provided on the lower surface of the solid electrolytic substrate 100. The solid electrolytic substrate 100 and the insulating layer 101 have through holes 108 and 109, respectively. The through holes 108 and 109 are continuous and filled with an electrically conductive material. The terminal 122 is connected to a terminal 113 provided on the upper surface of the insulating layer 101 via the conductive material filled in the through holes 108 and 109.

A spacer 15 is provided on the lower surface of the solid electrolytic substrate 100. The spacer is made of an alumina ceramic which is an electrically insulating and gas-imperious material. The spacer 15 has an elongated groove 151 defining the reference gas chamber 150. A longitudinal center of the spacer 15 is configured into a pair of protruding portions 165 which cooperatively fix the sensing element at a predetermined position in the housing (refer to FIG. 4).

A heater substrate 16 is provided on the lower surface of the spacer 15. A heater element 160 and a pair of leads 161 are interposed between the spacer 15 and the heater substrate 16. The heater element 160 generates heat when electric current is supplied via the leads 161.

The heater substrate 16 has through holes 164 filled with an electric conductive material. The leads 161 are connected to terminals 163 provided on an opposite surface of the heater substrate 16 via the conductive material filled in the through holes 164.

Figure 4:
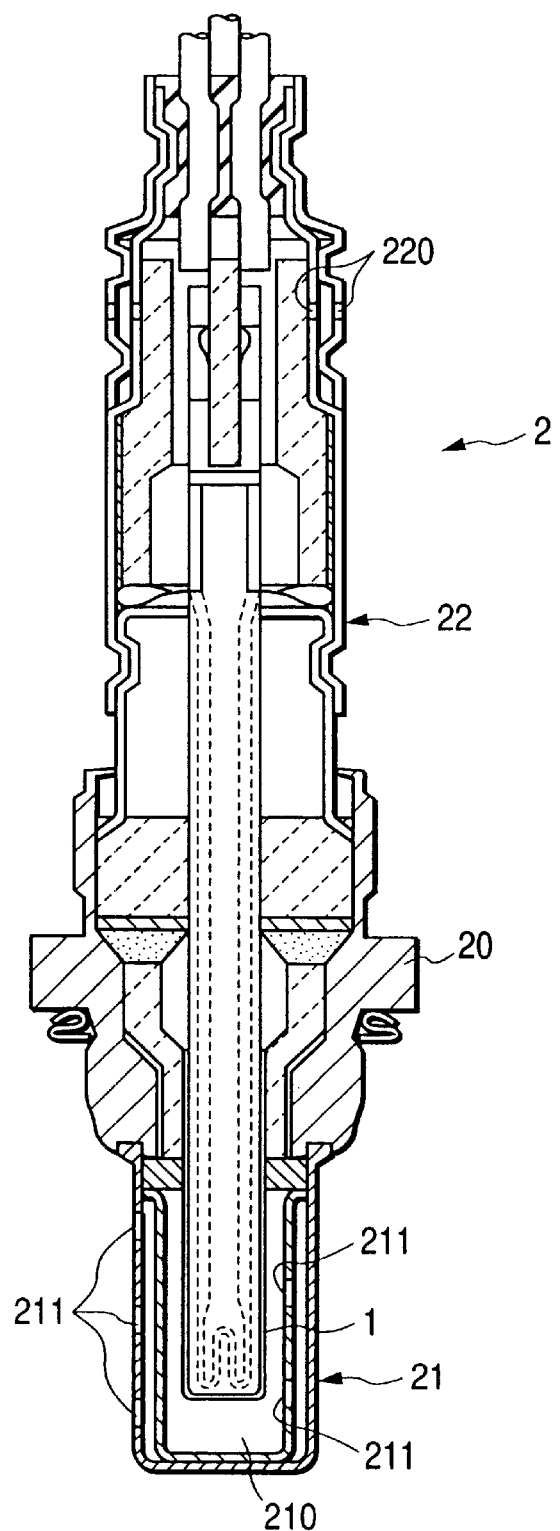
FIG. 4 is a vertical cross-sectional view showing an air-fuel ratio sensor in accordance with the preferred embodiment of the present invention.

FIG. 4 shows an air-fuel ratio sensor 2 incorporating the above-described multilayered air-fuel ratio sensing element 1. The air-fuel ratio sensor 2 comprises a metallic housing 20, a double cover 21 fixed to a front end of the metallic housing 20 so as to be exposed to the emission gas flowing in an exhaust gas passage (not shown) of an internal combustion engine (not shown), and an atmospheric cover 22 fixed to an opposite end of the metallic housing 20. The multilayered air-fuel ratio sensing element 1 is accommodated in the metallic housing 20.

The inside space of the double cover 21 serves as an emission gas chamber 210. The double cover 21 has numerous holes 211 for introducing the emission gas into the emission gas chamber 210.

The atmospheric cover 22 has numerous holes 220 for introducing the reference gas (i.e., air) to the reference gas chamber 150 of the multilayered air-fuel ratio sensing element 1 via the inside space of the atmospheric cover 22.

Next, the manufacturing method of the multilayered air-fuel ratio sensing element 1 will be explained.

First, green sheets are prepared to fabricate the heater substrate 16, the solid electrolytic substrate 100, the spacer 102, the porous diffusive resistor layer 13, and the gas shielding layer 14. The green sheets are formed by the doctor blade method or the extrusion method. The spacer 15 is fabricated by the injection molding. It is, however, possible to form the spacer 15 by digging a groove on the green sheet formed by the doctor blade method or the extrusion method.

Each green sheet is configured into a shape substantially identical with that shown in FIG. 2. The green sheet slightly shrinks when it is sintered. Thus, the size of the green sheet is designed to be slightly larger than the size of the sintered final product.

Next, an alumina paste is printed on the green sheet of the solid electrolytic substrate 100 to form the insulating layer 101. Then, a platinum paste is printed on the insulating layer 101 and the opposite surface of the solid electrolytic substrate 100 to form the emission gas sensing electrode 11, the reference gas sensing electrode 12, the leads 111, 121 and the terminals 112, 122.

A tungsten or platinum paste is printed on the green sheet of the heater substrate 16 to form the heater element 160 and the leads 161.

The platinum paste is printed on the insulating layer 101 to form the terminal 113 on the same surface as the lead 111 and the terminal 112.

Then, the fabricated green sheets are laminated as an integrated multilayered body as shown in FIG. 1 and sintered at the temperature of approximately 1,500° C. to 1,600° C. under a pressurized condition. Thus, the multilayered air-fuel ratio sensing element 1 is obtained as a final product installable into an air-fuel ratio sensor body.

Figure 13:
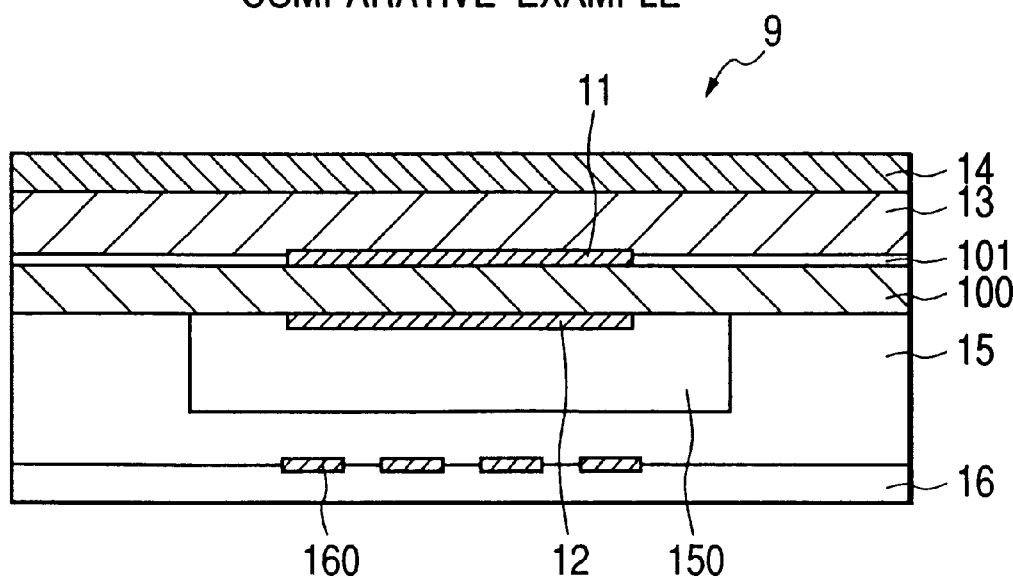
FIG. 13 is a lateral cross-sectional view showing an arrangement of a comparative multilayered air-fuel ratio sensing element.
Figure 14:
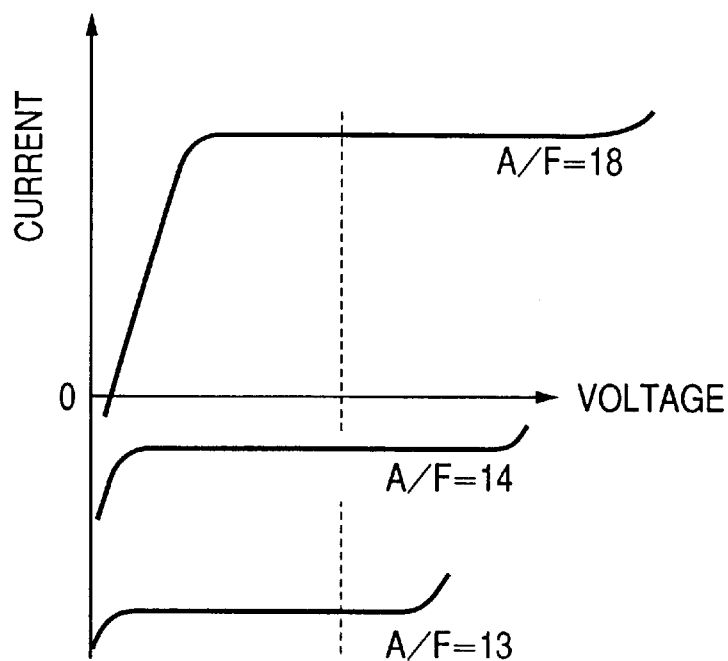
FIG. 14 is a graph showing the theoretical relationship between the applied voltage and the resultant current in respective air-fuel ratio values in a conventional multilayered air-fuel ratio sensing element.
Figure 15:
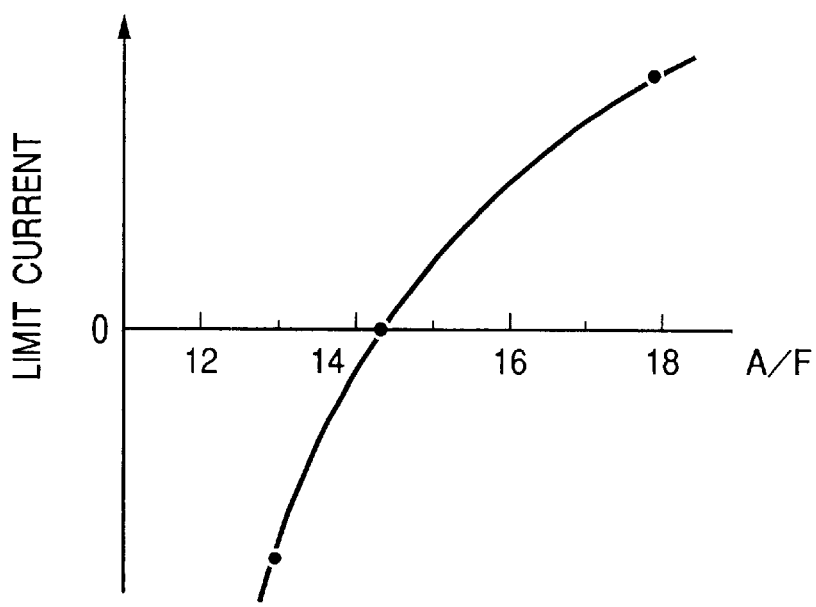
FIG. 15 is a graph showing the theoretical relationship between the limit current value and the air-fuel ratio in the conventional multilayered air-fuel ratio sensing element.

The performances of the multilayered air-fuel ratio sensing element of the above-described embodiment were evaluated in comparison with a comparative example shown in FIG. 13.

A comparative multilayered air-fuel ratio sensing element 9 shown in FIG. 13 has the same arrangement as that of the multilayered air-fuel ratio sensing element 1 shown in FIG. 1 except for the hollow space 10. Namely, the comparative sensing element 9 has no spacer 102 with the aperture 104 defining the hollow space 10.

For the evaluation tests, each of the multilayered air-fuel ratio sensing elements 1 and 9 was assembled in the air-fuel ratio sensor 2 shown in FIG. 4. The air-fuel ratio sensor 2 was installed in the exhaust gas passage of an internal combustion engine driven at a constant air-fuel ratio. A direct-current power source was connected to the air-fuel ratio sensor 2 to supply electric power to the built-in heater element 160. Thus, the sensing element was maintained at a desirable activated temperature.

Next, an oscillator was connected between the terminals 112 and 113 of each sensing element. A 10–100 mHz voltage having a sawtooth or sine waveform was applied between the terminals 112 and 113. FIGS. 5 through 8 show the measured data obtained from the evaluation tests.

Figure 5:
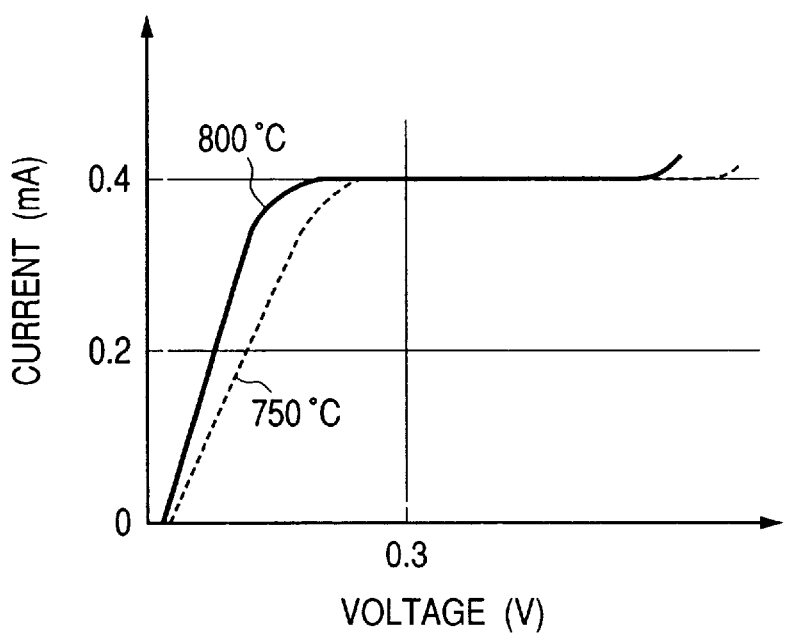
FIG. 5 is a graph showing the relationship between the voltage, current and temperature in the multilayered air-fuel ratio sensing element in accordance with the preferred embodiment of the present invention.
Figure 7:
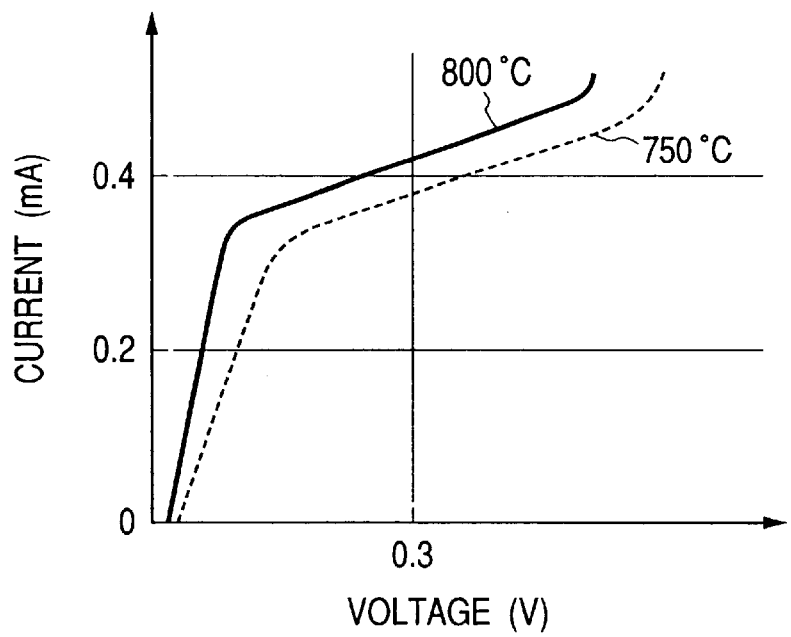
FIG. 7 is a graph showing the relationship between the voltage, current and temperature in a comparative multilayered air-fuel ratio sensing element.

Each of FIGS. 5 and 7 shows the relationship between the voltage applied to the sensing element and a resultant sensing current. The sensing current is measured between the emission gas sensing electrode 11 and the reference gas sensing electrode 12.

Figure 6:
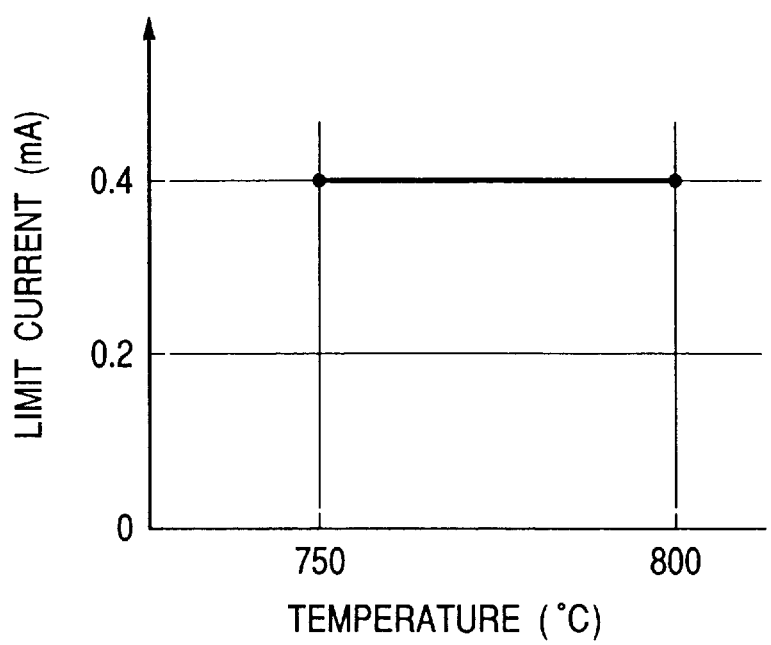
FIG. 6 is a graph showing the relationship between the limit current and temperature in the multilayered air-fuel ratio sensing element in accordance with the preferred embodiment of the present invention.
Figure 8:
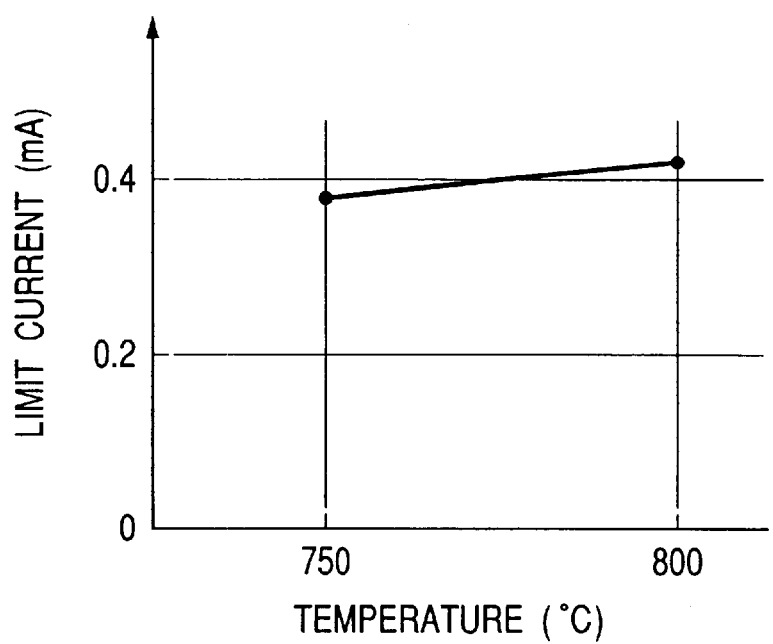
FIG. 8 is a graph showing the relationship between the limit current and temperature in the comparative multilayered air-fuel ratio sensing element.

Each of FIGS. 6 and 8 shows the limit current values measured at respective temperatures of 750° C. and 800° C. when the applied voltage is constant (0.3 V).

FIGS. 5 and 6 relate to the multilayered air-fuel ratio sensing element 1 having the arrangement in accordance with the present invention. As apparent from FIGS. 5 and 6, it is confirmed that there is a clear flat limit current region where the sensing current remains constant irrespective of the increase of the voltage applied to the multilayered air-fuel ratio sensing element 1. The limit current value is constant irrespective of the temperature change.

FIGS. 7 and 8 relate to the comparative multilayered air-fuel ratio sensing element 9. As apparent from FIGS. 7 and 8, it is confirmed that there is no flat limit current region and the limit current value varies in accordance with the temperature change.

From the measured data shown in FIGS. 5 to 9, it is apparent that the flat limit current region is surely obtained by providing the hollow space 10.

The functions and effects of the multilayered air-fuel ratio sensing element 1 will be explained hereinafter.

The emission gas reaches the hollow space 10 via the porous diffusive resistor layer 13. The emission gas is ionized on the emission gas sensing electrode 11, causing the oxygen ion current. In this case, the emission gas is uniformly mixed in the hollow space 10. In other words, the oxygen gas concentration does not fluctuate in the vicinity of the emission gas sensing electrode 11.

Accordingly, the present invention provides the multilayered air-fuel ratio sensing element 1 having an optimized relationship between the applied voltage and the sensing current. As shown in FIG. 5, the flat limit current region appears clearly with the limit current value proportional to the measured air-fuel ratio. Thus, the air-fuel ratio can be accurately measured.

The diffusion speed in the diffusive resistor layer 13 is less dependent to the temperature since the diffusive resistor layer 13 is made of a porous material. The limit current value seldom vary in response to the temperature change as shown in FIG. 6.

As described above, the multilayered air-fuel ratio sensing element 1 is compact in size. The thickness of the porous diffusive resistor layer 13 is 200 μm which is very thin. However, the emission gas is temporarily stored in the hollow space 10. This is effective to provide the flat limit current region.

In this manner, the present invention provides a multilayered air-fuel ratio sensing element which is compact in size and is capable of detecting the air-fuel ratio accurately irrespective of the temperature change or the power source voltage change.

The relationship between the volume of the hollow space 10 and the response time of the multilayered air-fuel ratio sensing element 1 was also evaluated.

Figure 9:
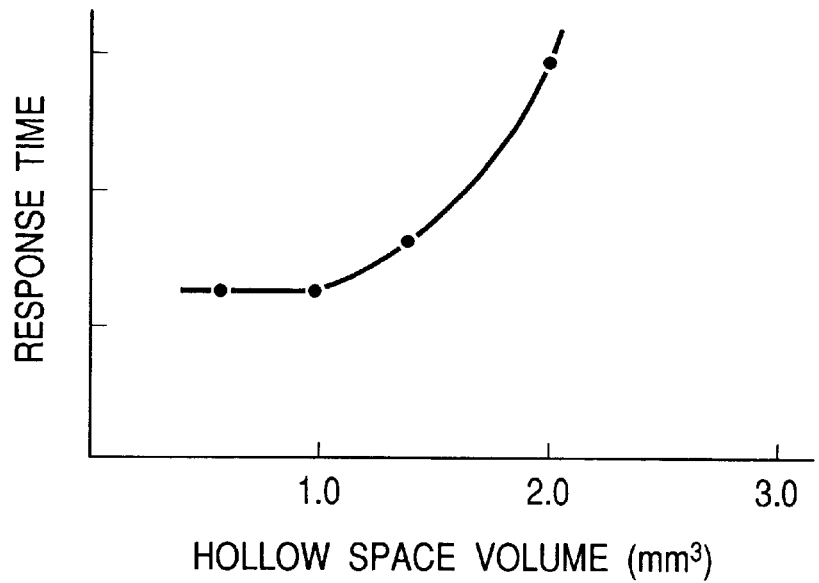
FIG. 9 is a graph showing the relationship between the hollow space volume and the response time of the multilayered air-fuel ratio sensing element in accordance with the preferred embodiment of the present invention.

A constant voltage for producing the limit current region was applied between the terminals 112 and 113 of the air-fuel ratio sensor installed in the engine exhaust passage. Under this condition, the air-fuel ratio of the internal combustion engine was changed in a stepwise manner to measure the change in the sensing current. FIG. 9 shows the measured result. An abscissa of FIG. 9 represents a volume of the hollow space per 10 $mm^2$ surface area of the emission gas sensing electrode 11.

It is confirmed form FIG. 9 that the multilayered air-fuel ratio sensing element 1 has an appropriate response time for controlling the air-fuel ratio of the internal combustion engine when the volume of the hollow space 10 is equal to or smaller than 3 $mm^3$ per 10 $mm^2$ surface area of the emission gas sensing electrode 11.

When the response time is long, the engine combustion control is significantly delayed. Both the fuel economy and the emission purification efficiency will be worsened.

Figure 10:
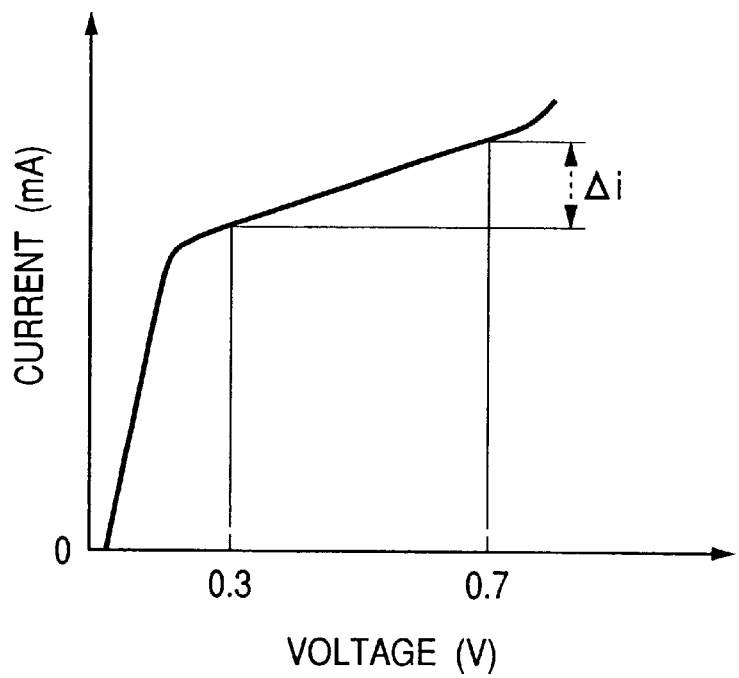
FIG. 10 is a graph showing a current variation Δi in accordance with the preferred embodiment of the present invention.

Next, the relationship between the height of the hollow space 10 and Δi was measured from the multilayered air-fuel ratio sensing element 1. In this case, Δi represents a current variation responsive to a 0.4V (from 0.3V to 0.7V) variation in the voltage applied to the multilayered air-fuel ratio sensing element 1, as shown in FIG. 10. The height of the hollow space 10 is a distance between the upper surface of the emission gas sensing electrode 11 and the lower surface of the porous diffusive resistor layer 13, as shown in FIG. 1.

Figure 11:
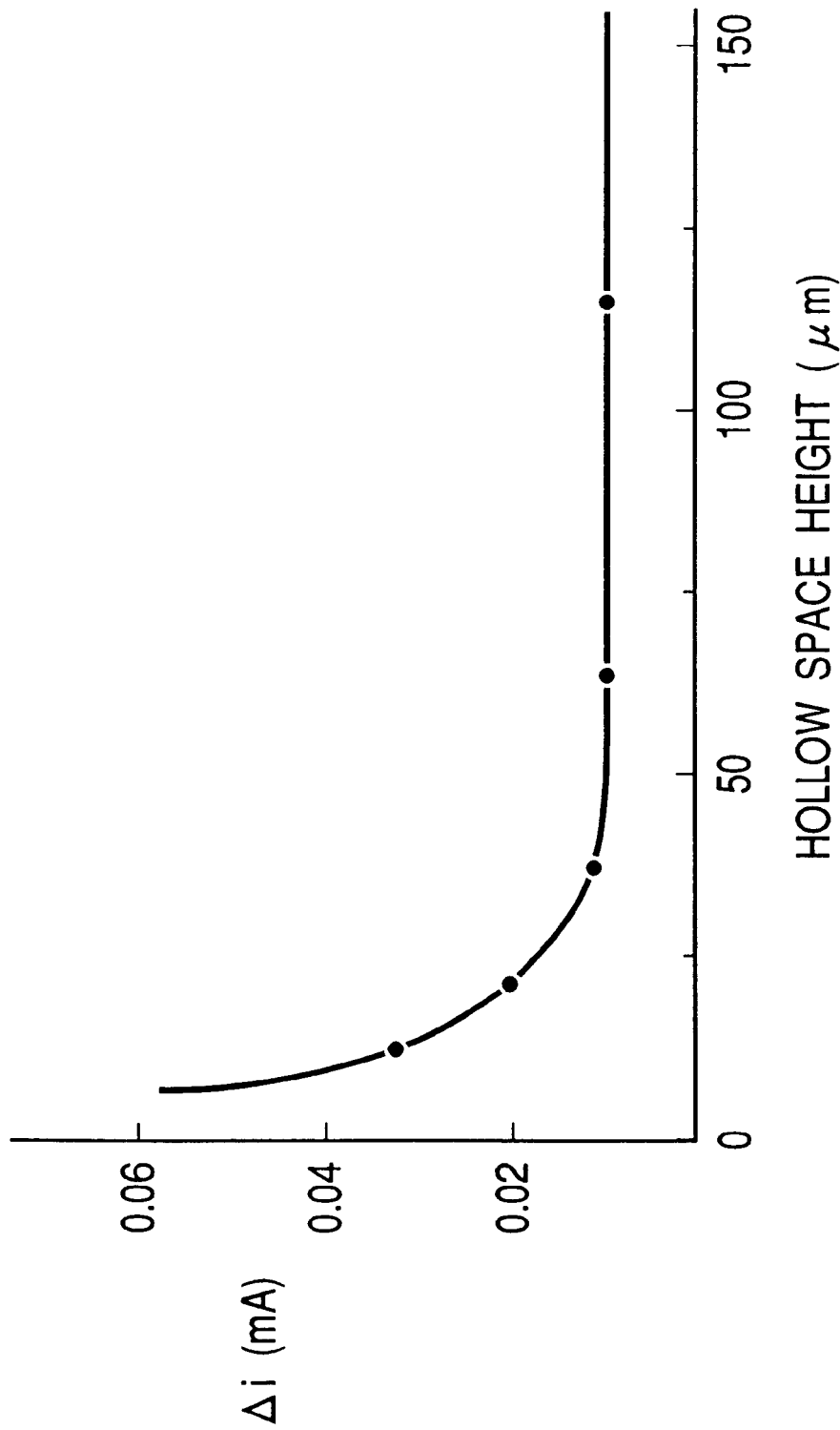
FIG. 11 is a graph showing the relationship between the hollow space height and the current variation Δi in accordance with the preferred embodiment of the present invention.

FIG. 11 shows the relationship between the height of the hollow space 10 and current variation Δi obtained by measuring a resultant sensing current under the test conditions that the element temperature is maintained at 750° C. and the 10–100 mHz voltage having a sawtooth or sine waveform is applied between the terminals 112 and 113 by the oscillator.

As apparent from FIG. 11, the current variation Δi is less than 0.02 mA when the height of the hollow space is equal to or larger than 20 μm. In other words, it is confirmed that an appropriate flat limit current region can be obtained when the hollow space height is equal to or larger than 20 μm.

However, the current variation Δi increases abruptly when the height of the hollow space 10 is less than 20 μm. In this case, the limit current region is no longer flat. The air-fuel ratio measuring accuracy is deteriorated.

Figure 12:
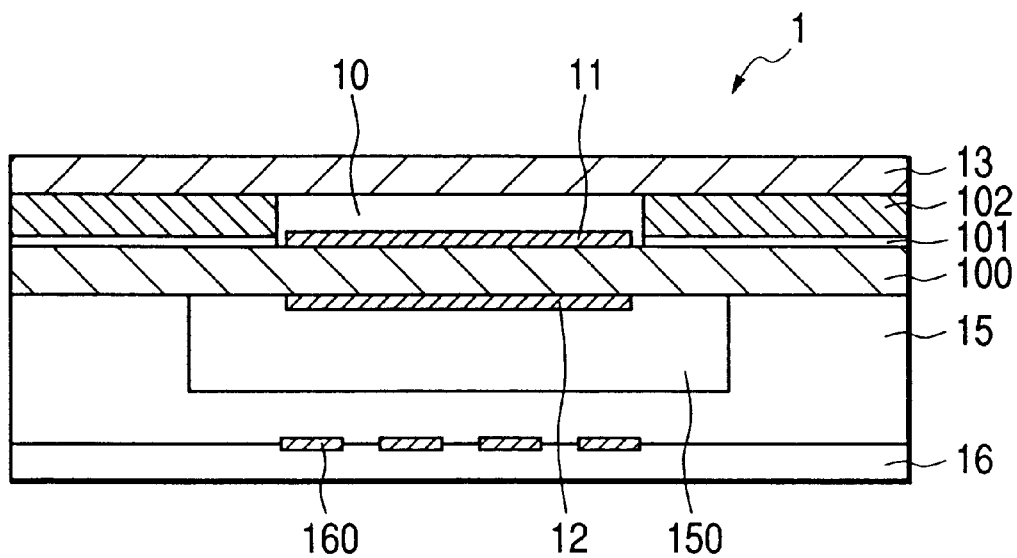
FIG. 12 is a lateral cross-sectional view showing an arrangement of a multilayered air-fuel ratio sensing element in accordance with another preferred embodiment of the present invention.

According to the above-described embodiment, the gas shielding layer 14 is provided on the porous diffusive resistor layer. However, the functions and effects of the present invention can be obtained even when the gas shielding layer is omitted as shown in FIG. 12.

Figure 3B:
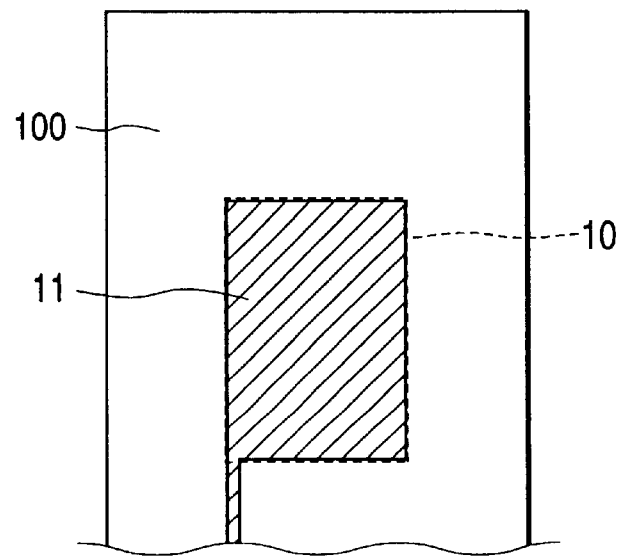

Furthermore, it is possible to completely equalize the surface area of the emission gas sensing electrode 11 with the transverse area of the hollow space 10 as shown in FIG. 3B.

As described above, one aspect of the present invention provides the multilayered air-fuel ratio sensing element comprising the solid electrolytic substrate having oxygen ion conductivity. The measuring gas sensing electrode (i.e., emission gas sensing electrode) is provided on one surface of the solid electrolytic substrate so as to be exposed to the measuring gas. The reference gas sensing electrode is provided on another surface of the solid electrolytic substrate so that the reference gas sensing electrode is exposed to the reference gas introduced into the reference gas chamber. The measuring gas sensing electrode is covered by the porous diffusive resistor layer. And, the multilayered air-fuel ratio sensing element of the present invention is characterized in that the hollow space is provided between the measuring gas sensing electrode and the porous diffusive resistor layer.

The transverse area of the hollow space, extending parallel to the measuring gas sensing electrode, is substantially identical with or slightly wider than the surface area of the measuring gas sensing electrode. When seen from the direction normal to the surface of the measuring gas sensing electrode as shown in FIGS. 3A and 3B, the measuring gas sensing electrode completely overlaps with the hollow space.

With this arrangement, the emission gas flows into the hollow space via the porous diffusive resistor layer and is mixed in the hollow space before it reaches the measuring gas sensing electrode.

Figure 16:
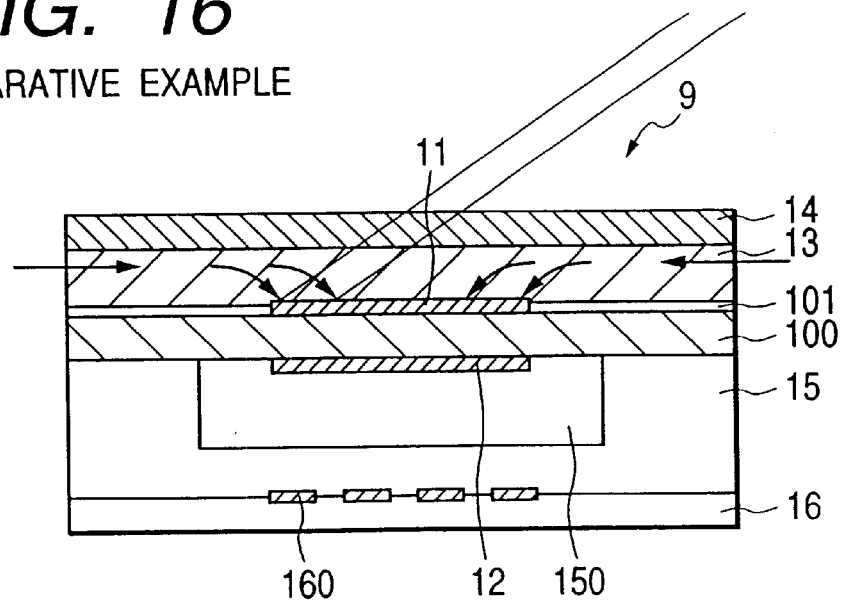
FIG. 16 is a lateral cross-sectional view showing the emission gas flow in the comparative multilayered air-fuel ratio sensing element shown in FIG. 13.

More specifically, according to the comparative example shown in FIG. 13, the emission gas flowing in the porous diffusive resistor layer reaches the measuring gas sensing electrode with a different time lag depending on the reaching point of each emission gas flow (refer to FIG. 16). Accordingly, undesirable distribution of the measuring gas concentration is formed along the surface of the measuring gas sensing electrode.

Figure 17:
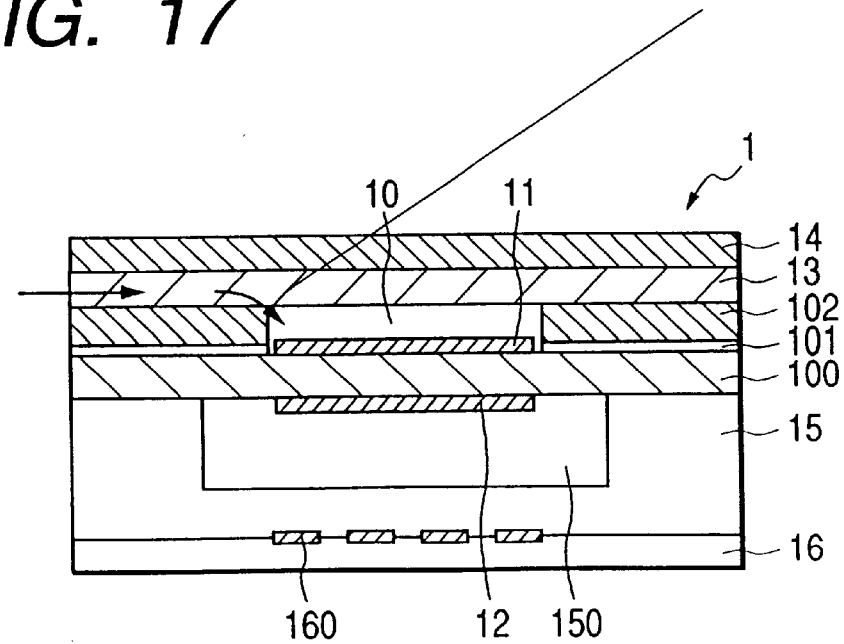
FIG. 17 is a lateral cross-sectional view showing the emission gas flow in the multilayered air-fuel ratio sensing element shown in FIG. 1.

On the other hand, as shown in FIG. 17, according to the present invention, the measuring gas is temporarily stored in the hollow space before the measuring gas reaches the measuring gas sensing electrode. In other words, the hollow space of the present invention serves as a buffer for temporarily storing the measuring gas and uniformly mixing the measuring gas. Thus, the undesirable distribution of the measuring gas concentration is eliminated. The measuring gas concentration does not fluctuate in the vicinity of the measuring gas sensing electrode. Accordingly, the present invention provides the multilayered air-fuel ratio sensing element having an optimized relationship between the applied voltage and the sensing current. As shown in FIG. 5, the flat limit current region appears clearly with the limit current value proportional to the measured air-fuel ratio. Thus, the air-fuel ratio can be accurately measured.

Preferably, the porous diffusive resistor layer is made of the ceramic selected from the group of alumina, zirconia, and $Al_2O_3$—MgO spinel.

Furthermore, as shown in FIG. 11, it is preferable that the hollow space has a height in a range of 20 $\mu$m to 150 $\mu$m. When the height (i.e., clearance between the measuring gas sensing electrode and the porous diffusive resistor layer) is lower than 20 $\mu$m, it is difficult to obtain a flat limit current region. When the height is higher than 150 $\mu$m, the response of the multilayered air-fuel ratio sensing element is worsened.

It is preferable that the volume of the hollow space is 0.2 to 3.0 $mm^3$ per 10 $mm^2$ surface area of the measuring gas sensing electrode.

When the hollow space volume is less than 0.2 $mm^3$, the effects of the present invention cannot be obtained. When the hollow space volume is larger than 3.0 $mm^3$, the response of the multilayered air-fuel ratio sensing element is worsened. A required volume of the hollow space increases with increasing surface area of the measuring gas sensing electrode.

It is also preferable that the porous diffusive resistor layer has a porous rate of 3 to 15%.

When the porous rate is less than 3%, the measuring gas cannot flow smoothly in the porous diffusive resistor layer. The measuring gas amount introduced into the hollow space is insufficient for measuring the air-fuel ratio accurately. The response of the multilayered air-fuel ratio sensing element is worsened. When the porous rate is larger than 15%, the resultant current value becomes excessively large compared with the gas ion pumping ability of the measuring gas sensing electrode. The resultant limit current region is not flat.

It is also preferable that at least part of the surface of the porous diffusive resistor layer is covered by the gas shielding layer. With the provision of the gas shielding layer, the measuring gas introduced into the hollow space can be adequately restricted. In other words, it becomes possible to control the limit current value of the multilayered air-fuel ratio sensing element. The sensor element can be downsized without sacrificing the prompt activation ability.

It is further preferable that the gas shielding layer is provided at a position opposing to the measuring gas sensing electrode. The gas shielding layer adequately regulates the flow of the measuring gas in the porous diffusive resistor layer. The measuring gas diffuses in the transverse direction along the gas shielding layer. It becomes possible to simply control the limit current value by changing the thickness of the diffusive resistor layer and the width of the sensing element.

It is further preferable that the gas shielding layer is made of a gas impervious ceramic. The gas shielding layer made of ceramic can be sintered together with the sensing element. Thus, the manufacturing process can be simplified. The durability of the air-fuel ratio sensor is improved.

It is further preferable that the gas shielding layer extends along the surface of the porous diffusive resistor layer in an opposed relationship with the measuring gas sensing electrode via the porous diffusive resistor layer. With this arrangement, the measuring gas introduced into the porous diffusive resistor layer flows in parallel with the gas shielding layer and reaches the measuring gas sensing electrode via the hollow space.

The porous diffusive resistor layer can be fabricated by laminating a green sheet on the solid electrolytic substrate, via the spacer forming the hollow space, and sintering an integrally laminated body.

Another aspect of the present invention provides the method for manufacturing a multilayered air-fuel ratio sensing element. In a first step, a plurality of green sheets are prepared to fabricate the solid electrolytic substrate, the spacer and the porous diffusive resistor layer. In a second step, the plurality of green sheets are successively laminated to form an integrated multilayered body with a hollow space between the solid electrolytic substrate and the porous diffusive resistor layer. In a third step, the integrated multilayered body is sintered.

Preferably, the manufacturing method further comprises a step of additionally laminating the green sheet serving as the gas shielding layer on the porous diffusive resistor layer before the integrated multilayered body is sintered.

This invention may be embodied in several forms without departing from the spirit of essential characteristics thereof. The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A multilayered air-fuel ratio sensing element comprising:

a solid electrolytic substrate having oxygen ion conductivity;

a measuring gas sensing electrode provided on one surface of said solid electrolytic substrate so as to be exposed to a measuring gas;

a reference gas sensing electrode provided on another surface of said solid electrolytic substrate so that said reference gas sensing electrode is exposed to a reference gas introduced into a reference gas chamber;

a porous diffusive resistor layer covering said measuring gas sensing electrode;

a hollow space provided between said measuring gas sensing electrode and said porous diffusive resistor layer; and a substantially gas impervious shielding layer covering at least part of an outer surface of said porous diffusive resistor layer provided outside said hollow space.

2. The multilayered air-fuel ratio sensing element in accordance with claim 1, wherein said hollow space has a volume of 0.2 to 3.0 mm$^3$ per 10 mm$^2$ surface area of said measuring gas sensing electrode.

3. The multilayered air-fuel ratio sensing element in accordance with claim 1, wherein said porous diffusive resistor layer has a porous rate of 3 to 15%.

4. The multilayered air-fuel ratio sensing element in accordance with claim 1, wherein said shielding layer is provided at a position opposing to said measuring gas sensing electrode.

5. The multilayered air-fuel ratio sensing element in accordance with claim 1, wherein said shielding layer is made of a gas-impervious ceramic.

6. The multilayered air-fuel ratio sensing element in accordance with claim 1, wherein said shielding layer is disposed on at least a portion of said porous diffusive resistor layer so that the measuring gas introduced into said porous diffusive resistor layer flows in parallel with said shielding layer and reaches said measuring gas sensing electrode via said hollow space.

7. The multilayered air-fuel ratio sensing element in accordance with claim 1, wherein said hollow space has a height in a range of 20 to 150 $\mu$m.

8. The multilayered air-fuel ratio sensing element in accordance with claim 1, wherein said porous diffusive resistor layer is fabricated by laminating a green sheet on said solid electrolytic substrate and sintering an integrally laminated body.

9. A multilayered air-fuel ratio sensing element comprising:

a solid electrolytic substrate having oxygen ion conductivity;

a measuring gas sensing electrode provided on a first surface of said solid electrolytic substrate so as to be exposed to a measuring gas;

a reference gas sensing electrode provided on a second surface of said solid electrolytic substrate so that said reference gas sensing electrode is exposed to a reference gas introduced into a reference gas chamber;

a spacer layer disposed on said first surface, said spacer layer having an aperture formed therein;

a porous diffusive resistor layer disposed on said spacer layer such that a hollow space is bounded by said solid electrolytic substrate, walls of said aperture, and said porous diffusive resistor layer, said measuring gas electrode being disposed within said hollow space with an amount of space between said measuring gas electrode and said porous diffusive resistor layer; and a substantially gas impervious ceramic shielding layer disposed on said porous diffusive resistor layer, said shielding layer cooperating with said porous diffusive resistor layer to constrain the flow of the measuring gas into said hollow space.

* * * * *